US010639248B2

(12) United States Patent
Lo

(10) Patent No.: US 10,639,248 B2
(45) Date of Patent: May 5, 2020

(54) SOLID WATER PARTICLE COMPOSITION AND METHOD OF USE FOR ENHANCING COSMETIC ITEMS AND CONSUMABLE LIQUIDS

(71) Applicant: Shui Yin Lo, Pasadena, CA (US)

(72) Inventor: Shui Yin Lo, Pasadena, CA (US)

(*) Notice: Subject to any disclaimer, the term of this patent is extended or adjusted under 35 U.S.C. 154(b) by 0 days.

(21) Appl. No.: 15/391,388

(22) Filed: Dec. 27, 2016

(65) Prior Publication Data

US 2017/0189284 A1    Jul. 6, 2017

Related U.S. Application Data

(60) Provisional application No. 62/273,170, filed on Dec. 30, 2015.

(51) Int. Cl.
*A61K 8/19* (2006.01)
*A61Q 19/08* (2006.01)
*A23L 2/52* (2006.01)

(52) U.S. Cl.
CPC ............... *A61K 8/19* (2013.01); *A23L 2/52* (2013.01); *A61Q 19/08* (2013.01); *A23V 2002/00* (2013.01)

(58) Field of Classification Search
None
See application file for complete search history.

(56) References Cited

U.S. PATENT DOCUMENTS

2008/0139674 A1*  6/2008  Archambeau ........ A61K 9/0048
                                                                514/789

* cited by examiner

*Primary Examiner* — Carlos A Azpuru
*Assistant Examiner* — Casey S Hagopian

(57) ABSTRACT

A solid water particle composition and method of use enhances the efficacy of a cosmetic item, a consumable liquid, and an organic liquid. The composition is based on a solid water particle phase of water. The composition consists of adding solid water particle composition to cosmetic item and a consumable liquid with or without replacing the pure water in the cosmetic item and consumable liquid, while at least one indigenous ingredient in the cosmetic item and consumable liquid remains substantially the same. The cosmetic item includes a cosmetic face mask and a cosmetic face cream. The consumable liquid includes an herbal drink. The solid water particle composition can also replace pure water in an organic liquid, such as alcoholic drink, organic solvent, liquid fuel, and paint. The cosmetic items and consumable liquids are enhanced by replacing pure water, with water having solid water particles and leaving ingredients substantially the same.

3 Claims, 3 Drawing Sheets

SOLID WATER PARTICLE COMPOSITION AND METHOD OF USE FOR ENHANCING COSMETIC ITEMS AND CONSUMABLE LIQUIDS

CROSS REFERENCE OF RELATED APPLICATIONS

This application claims the benefits of U.S. provisional application No. 62/273,170 filed Dec. 30, 2015 and entitled SOLID WATER PARTICLE COMPOSITION AND METHOD OF USE FOR ENHANCING COSMETIC ITEMS AND CONSUMABLE LIQUIDS, which provisional application is incorporated by reference herein in its entirety.

FIELD OF THE INVENTION

The present invention relates generally to a solid water particle composition and method of use for enhancing cosmetic items and consumable liquids. More so, a composition based on a solid water particle phase of water is configured to replace pure water from a cosmetic item and a consumable liquid with a solid water particle composition, while maintaining at least one indigenous ingredient in the cosmetic item and the consumable liquid substantially the same; whereby the solid water particle is a unique phase of water that triggers self-healing and provides myriad other healthful benefits to the body; whereby replacing pure water with the solid water particle enhances the cosmetic item and the consumable liquid.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Typically, cosmetic items are substances or products used to enhance the appearance or fragrance of the body. Many cosmetic items are designed for use of applying to the face and hair. Cosmetic items are generally mixtures of chemical compounds; some being derived from natural sources (such as coconut oil), and some being synthetics. Common cosmetic items may include lipstick, mascara, eye shadow, foundation, rouge, skin cleansers, skin lotions, shampoo, hairstyling products, perfume, and cologne.

It is known that water clusters, method of their manufacture as well as methods of their manufacture and use are known in the art. They are disclosed for example in Proceedings of First International Conference of the Physical, Chemical and Biological Properties of Stable Water Clusters, edited by B. Bonavita, S. Y. Lo, World Scientific 1997, and in U.S. Pat. Nos. 5,800,576; 5,997,590; U.S. patent application publication 2006/0110418, international patent application publication WO 2009/04912, U.S. patent application publication 2005/0270896, U.S. Pat. No. 6,487,994, U.S. patent application publication 2004/0025416.

It is known that there exists a state or phase of water that contains water molecules which have gone solid at room temperature. In this state, the liquid phase of the water under a particular set of circumstances can condense into tiny solid water particles. These solid water particles have increased surface area and filtering capacity, which helps to trigger a self-healing process in the body. Further, it is recognized in the art that a solid water particle that exists in pure water, and that particle is itself made of pure water. There are no additives or added chemical compounds of any kind in such a water composition. It is ultra-pure, often many times cleaner and with fewer contaminates than distilled or purified water. It is this purity and the larger surface area provided by the solid water particle that enables this enhanced beauty and health benefits.

Other proposals have involved enhancing cosmetic items and consumable liquids. The problem with these compositions is that they do not integrate solid water particles in place of pure water. Also, the indigenous ingredients are altered. Even though the above cited enhancing compositions meets some of the needs of the market, a composition based on a solid water particle phase of water that is added to a cosmetic item and a consumable liquid with or without replacing water in the cosmetic item and the consumable liquid while maintaining at least one indigenous ingredient in the cosmetic item and the consumable liquid substantially the same is still desired.

SUMMARY

Illustrative embodiments of the disclosure are generally directed to a solid water particle composition and method of use. The solid water particle composition and method of use enhances the efficacy of a cosmetic items and a consumable liquid. The solid water particle composition is based on a solid water particle phase of water. The composition is added to a cosmetic item and a consumable liquid with or without replacing the water in the cosmetic item and the consumable liquid, while at least one indigenous ingredient in the cosmetic item and the consumable liquid remains substantially the same.

For example, the cosmetic item may include a cosmetic face mask and a cosmetic face cream. The consumable liquid includes an herbal drink. The solid water particle composition can also replace pure water in an organic liquid, such as an alcoholic drink, an organic solvent, a liquid fuels, and a paint. Thus, the present invention enhances cosmetic items and consumable liquids fabricated from indigenous ingredients by replacing pure water component of the indigenous materials with water consisting of solid water particles.

One aspect of a method of adding solid water particle composition to enhance a cosmetic item and a consumable liquid, comprises: obtaining a cosmetic item and a consumable liquid, the cosmetic item and the consumable liquid comprising pure water and at least one indigenous ingredient; with or without removing pure water from the cosmetic item and the consumable liquid; retaining at least one indigenous ingredient in the cosmetic item and the consumable liquid; adding a solid water particle composition to the cosmetic item and the consumable liquid; and enhancing the health benefits of the cosmetic item and the consumable liquid.

In another aspect, the method further includes a step of at least partially removing pure water from an organic liquid, the organic liquid including at least one member selected from the group consisting of: alcoholic drinks, organic solvent, liquid fuels, and paints.

In another aspect, the method further includes a step of adding the solid water particle based composition to the organic liquid.

In another aspect, the solid water particle composition is configured into the form of a liquid, the liquid configured to drip into the eyes, the nose, the ears, and the belly button.

In another aspect, the solid water particle composition is configured into the form of a mist, the mist configured to spray into at least one of the following: the hair for enhancing the health of the hair, the nose to help relief asthma, and the eyes for clarity and health.

In another aspect, the at least one indigenous ingredient includes at least one member selected from the group consisting of: anti-aging, anti-wrinkle, anti-oxidant, plant extracts, animal extracts.

In another aspect, the at least one indigenous ingredient is configured to provide a therapeutic effects on at least one member selected from the group consisting of: gout, migraine, arthritis, joint problem, rheumatoid arthritis, tumor, neck pain, back pain, high level of cholesterol, high blood pressure, high sugar level, and a chronic disease.

One aspect of a solid water particle composition for enhancing a cosmetic item, comprises: a cosmetic item, the cosmetic item comprising at least partially of solid water particles and at least one indigenous ingredient, whereby the solid water particles are configured to add to the cosmetic item with or without replacing pure water in the cosmetic item.

In another aspect, the cosmetic item includes at least one member selected from the group consisting of: a cosmetic face mask, a cosmetic cream, a cosmetic gel.

In another aspect, the cosmetic item is configured to be applied directly to at least a portion of the body, including: skin, face, fingers, toes, joints, and reproductive organs, skin of the penis, outside testicles, and female clitoris.

One aspect of a solid water particle composition for enhancing a consumable liquid, comprises: a consumable liquid, the consumable liquid comprising at least partially of solid water particles and at least one indigenous ingredient, whereby the solid water particles are configured to add to consumable liquid with or without replacing some pure water in the consumable liquid.

In another aspect, the consumable liquid includes at least one member selected from the group consisting of: an herbal drink, a vitamin drink, herbs, vitamins, minerals, and ginseng.

In another aspect, the solid water particle composition is configured to add an organic liquid with or without replacing pure water in the organic liquid, the organic liquid including at least one member selected from the group consisting of: an alcoholic drink, an organic solvent, a liquid fuels, and a paint.

In another aspect, the alcoholic drink includes at least one member selected from the group consisting of: pure alcohol, wine, liquor, and beer.

In another aspect, the liquid fuel includes at least one member selected from the group consisting of: gasoline, diesel, jet fuel, and heavy oil.

In another aspect, the paint includes at least one member selected from the group consisting of: gross pain and acrylic paint.

One objective of the present invention is to provide a solid water particle composition add to a cosmetic item and a consumable liquid with or without replacing water in the cosmetic item and the consumable liquid to enhance the benefits of the cosmetic item and the consumable liquid.

Another objective is to provide a method for replacing pure water in the cosmetic item and the consumable liquid with a solid water particle composition.

Another objective is to provide a cosmetic face mask having the beautification benefits provided by solid water particles.

Another objective is to provide a cosmetic face cream having the beautification benefits provided by solid water particles.

Another objective is to provide an herbal liquid drink having the health benefits provided by solid water particles.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

Figure 1:
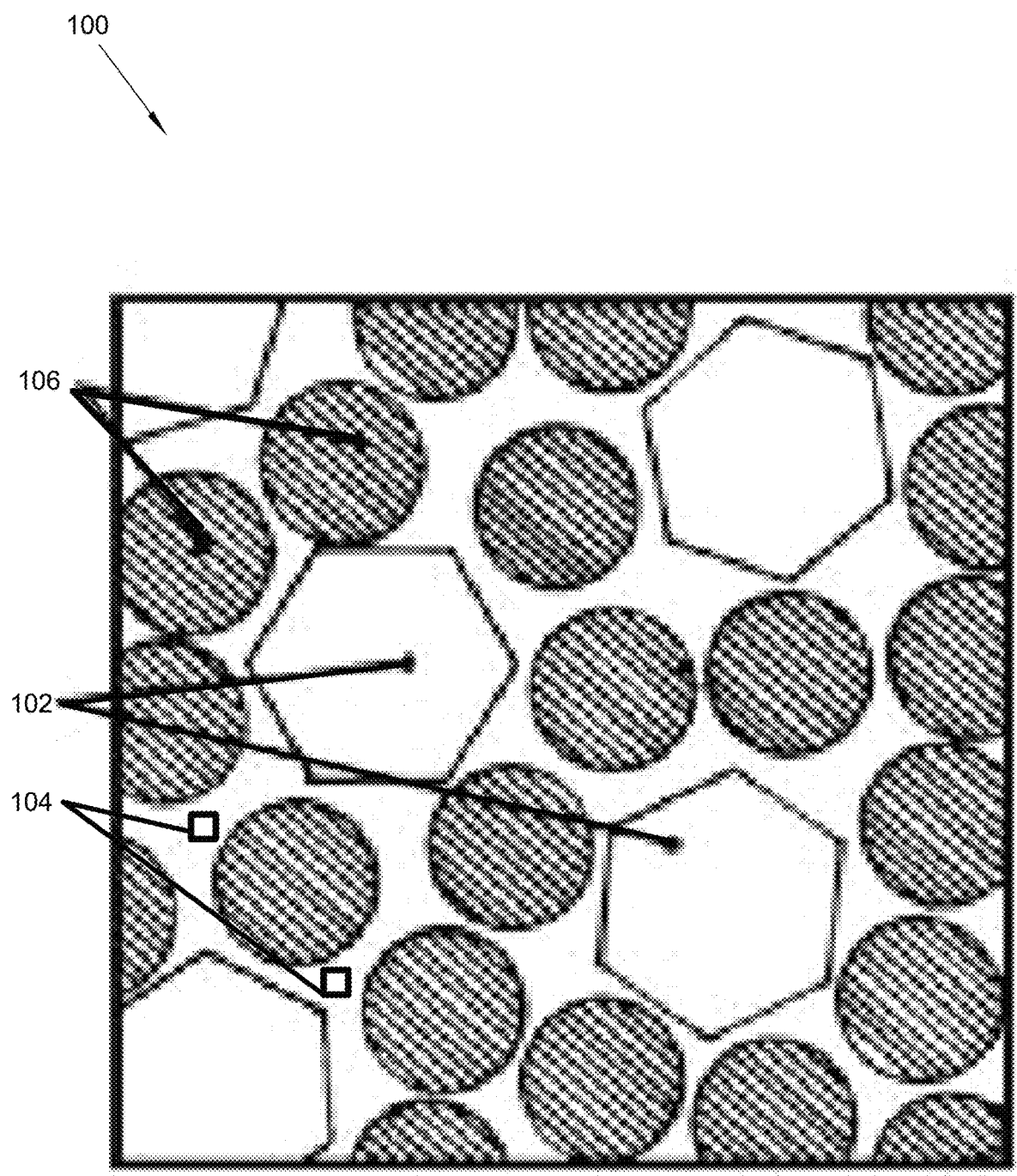
FIG. 1 illustrates a diagram of an exemplary solid water particle composition, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

Figure 2:
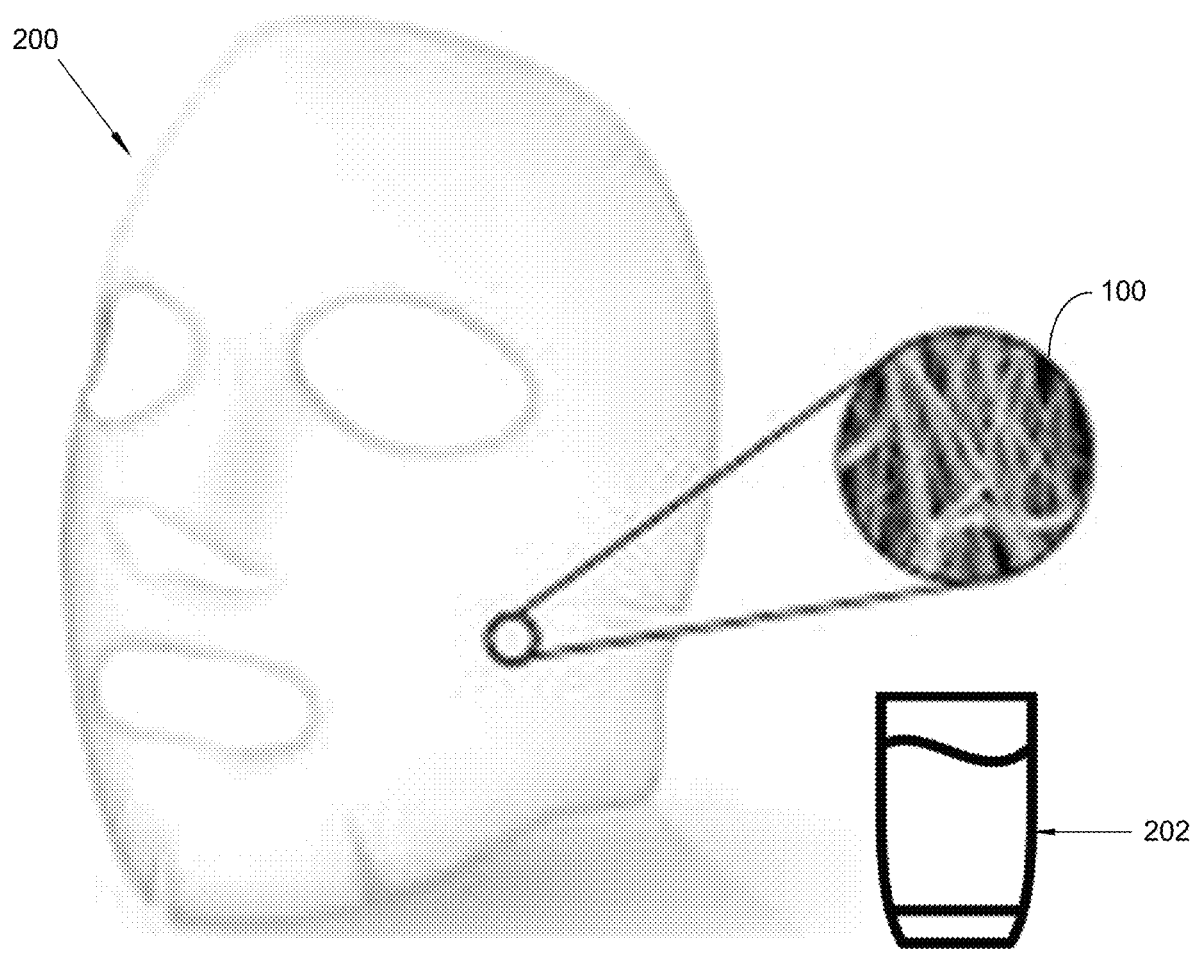
FIG. 2 illustrates a top view of an exemplary cosmetic item and a consumable liquid, in accordance with an embodiment of the present invention.
Figure 3:
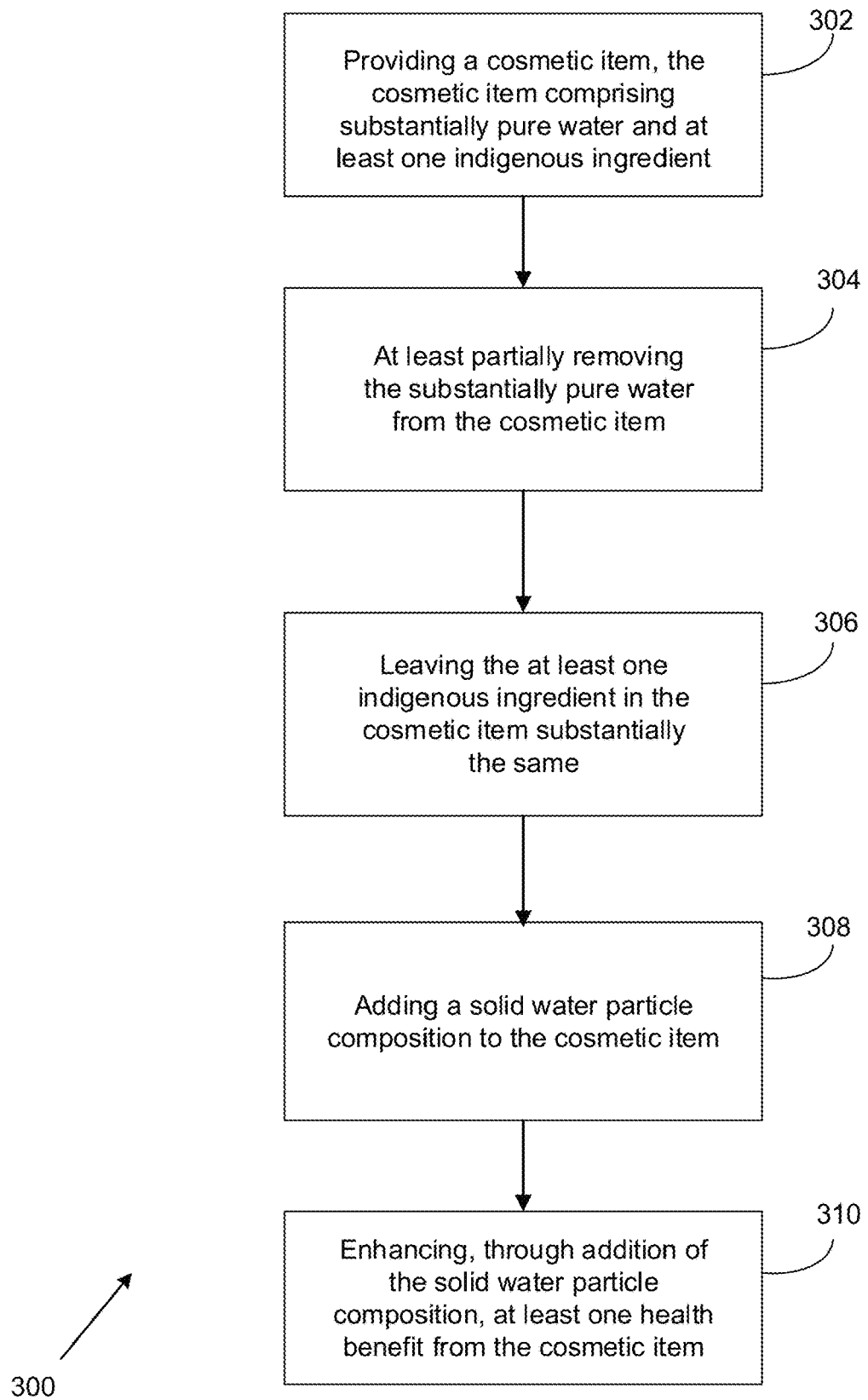
FIG. 3 illustrates a flowchart of an exemplary method of replacing pure water with a solid water particle composition, in accordance with an embodiment of the present invention.

In one embodiment of the present invention presented in FIGS. 1-3, a solid water particle composition 100 and method 300 of use is configured to enhance a cosmetic item 200 and a consumable liquid 202 that comprise at least one indigenous ingredient 104. The solid water particle composition 100, hereafter, "composition 100" is configured to be derived at least partially, from a solid water particle phase of water.

In one embodiment, the composition 100 may replace the substantially pure water 106 that is found in the cosmetic item 200 and the consumable liquid 202. Thus, while the composition 100 may or may not replace the pure water 106, the at least one indigenous ingredient 104 in the cosmetic item 200 and the consumable liquid 202 remain substantially the same. However, it is significant to note that the composition 100 may be added to the cosmetic item 200 and the consumable liquid 202 without removing the pure water 106.

Thus in essence, the present invention enables the formation of enhanced cosmetic items 200 and consumable liquids 202 that are at least partially fabricated from at least one indigenous ingredient 104, by replacing the substantially pure water 106 component of the indigenous ingredient 104 with a different water consisting of solid water particles 102.

As referenced in FIG. 1, and as those skilled in the art will recognize; there exists a state or phase of water that contains water molecules which have gone solid at room temperature. In this state, the liquid phase of the water under a particular set of circumstances can condense into tiny solid water particles 102. These solid water particles 102 have increased surface area and filtering capacity, which helps to trigger a self-healing process in the body. Thus, the present invention integrates the solid water particle 102 phase of water into the cosmetic item 200 and consumable liquid 202, so as to achieve the benefits thereof.

Further, it is recognized in the art that a solid water particle 102 that exists in pure water, and that particle 102 is itself made of pure water. There are no additives or added chemical compounds of any kind in such a water composition 100. It is ultra-pure, often many times cleaner and with fewer contaminates than distilled or purified water. It is this purity and the larger surface area provided by the solid water particle 102 that enables this enhanced beauty and health benefits.

Those skilled in the art will recognize that the solid water particle 102 is a unique phase of water that triggers self-healing and provides myriad other healthful benefits to the body. The present invention utilizes these beneficial characteristics of solid water particles 102 by adding to the cosmetic item 200 and the consumable liquid 202, either with or without replacing pure water in the cosmetic item or the consumable liquid with the composition 100 to enhance the cosmetic item 200 and the consumable liquid 202.

Looking back at FIG. 1, the solid water particle 102 used in the composition 100 is water insoluble. The solid water particle 102 may also consist of a compound whose solubility in water at 25° Celsius and at atmospheric pressure is less than 0.1%. The solid water particle 102 may have a number-average primary size ranging from 0.001 to 1000μηη. Those skilled in the art will recognize that the size of the particles 102 may be determined by transmission electron microscopy or by measuring the specific surface area by the BET method or using a laser particle sizer.

As illustrated in FIG. 2, the composition 100 may or may not replace the substantially pure water 106 in a cosmetic item 200. The cosmetic item 200 may include a cosmetic face mask. Thus, the composition 100 replaces the pure water in the cosmetic face mask. These face masks all have pure water, plus many natural plant ingredients, and chemicals. Each ingredient provides a beneficial effect on the skin such as anti-aging, reduce wrinkles, and brighten the skin. However in other embodiments, the cosmetic item 200 may include, without limitation, lipstick, mascara, eye shadow, foundation, rouge, skin cleansers, skin lotions, shampoo, hairstyling products, perfume, and cologne.

In one embodiment, the ingredients of a cosmetic face mask include at least one of the following: pure water; plant such as aloe Vera, mulberry; plant extracts such as Rosemary extract, Horsetail Extract, Pine Cone Extract, Lemon extract, Borage extract, Ginkgo Bilbo extract; Animal extracts such as honey, bee wax; herbs such as ginseng; chemicals such as Titanium Dioxide, potassium hydroxide, sodium hydroxide; trace elements such as Zinc and selenium; Vitamins, such as vitamin C, vitamin B, vitamin E; Amino acids; Enzymes; Algae-yeast complex. The pure water is substantially replaced by the composition 100, while the other components remain substantially the same. In this manner, the benefits of solid water particles 102 may be realized in the cosmetic face mask.

In one embodiment, the composition 100 may or may not replace the substantially pure water 106 in a cosmetic item 200, such as a face cream or face mask, shown in FIG. 2. Thus, the composition 100 replaces the pure water 106 in the cosmetic item 200. Those skilled in the art will recognize that facial creams often contains a great variety of substances that are claimed to promote healthy skin. Face creams generally comprise a substantial amount of pure water 106, plus many natural plant ingredients, and chemicals. Each ingredient provides a beneficial effect on the skin such as anti-aging, reduce wrinkles, and brightening the skin.

In one embodiment, the ingredient 104 in the cosmetic face cream includes at least one of the following: pure water 106; anti-aging component, Aloe Vera, Omega III, lecithin; anti-wrinkle component: Coconut oil, almond oil; anti-oxidant component: Coenzyme $Q_{10}$; Vitamins A, B, C, D, E; Minerals: Boron, Calcium, Chromium, Copper, Iodine, Iron, magnesium, manganese, Molybdenum, potassium, selenium, silica, Vanadium, Zinc; fragrance, such as rose extract; and preservatives. The pure water is substantially replaced by the composition 100, while the other components remain substantially the same. In this manner, the benefits of solid water particles 102 may be realized in the cosmetic face cream.

In one embodiment, the composition 100 replaces pure water in a consumable liquid 202. However, as discussed above, the composition 100 may be added to the cosmetic item 200 and the consumable liquid 202 without removing the pure water 106.

The consumable liquid 202 may include, without limitation, a healthful drink, an herbal liquid, and an organic liquid. The consumable liquids generally comprises pure water 106, plus at least one indigenous ingredient 104, which may include natural plant ingredients and chemicals. Each ingredient 104 provides a beneficial effect to the body when consumed. The pure water 106 is substantially replaced by the solid water particles 102 in the composition 100, while the other components remain substantially the same. In this manner, the benefits of solid water particles 102 may be realized in the consumable liquid 202.

One exemplary consumable liquid is a Vitamin C drink, which consists of a bottle of water with solid water particles 102 that has vitamin C dissolved in it. The drink may contain only herbs, such as: Renshen, Radix Ginseng; Xiyangshen: Radix Panacis Quinquefolii; and Duzhong Cortex Eucommiae. This herbal drink may contain a formula of several herbs that has certain therapeutic effects on diseases such as gout, migraine, arthritis, joint pain, dementia, Alzheimer's, tumors, rheumatoid arthritis, neck pain, back pain, cholesterol, high blood pressure, high sugar level, or any chronic diseases. The solid water particles 102 in the composition 100 further enhance these medical benefits.

Yet another exemplary consumable liquid is a ten-herb drink. Radix Codonopsis, Rhizoma Atractylodis Macrocephalae, Portae, Radix Glycyrrhizae, Radix Angelica Sinensis, Rhizoma Chuanxiong, Radix Paeoniae Alba, Radix Rehmanniae Preparata, Radix Astragali, Cortex Cinnamomi. Similarly, the pure water is substantially replaced by the composition 100, while the ten herbs remain substantially the same. In this manner, the benefits of solid water particles 102 may be realized in the ten-herb drink.

In one alternative embodiment, the composition 100 may be added to organic liquids and even non-consumable liquids to form a new class of solid water particle-organic liquid. These organic liquids and non-consumable liquids may include, without limitation: Alcoholic drinks, such as alcoholic beverages, liquor, wine, and beer; organic solvents; liquid fuels, such as heavy oil, diesel, gasoline, jet fuel; and paint. However it is significant to note that the present invention enables pure water 106 to be replaced with a solid water particle composition 100 for any cosmetic related item or liquid that consist, at least partially, of pure water.

FIG. 3 illustrates a flowchart of an exemplary method 300 of replacing pure water with a solid water particle composition 100 for enhancing a cosmetic item 200 and a consumable liquid. The method 300 is configured to be based on a solid water particle phase of water. In one embodiment, the composition 100 replaces pure water from a cosmetic item 200 and a consumable liquid.

In one embodiment, the composition 100 replaces the pure water with the solid water particles 102, while the other ingredients in the cosmetic item 200 and the consumable liquid remain substantially the same. Thus in essence, the method 300 enables the formation of enhanced cosmetic items 200 and consumable liquids fabricated from indigenous ingredients 104 by replacing, or not replacing, the pure water 106 component of the indigenous ingredients 104 with water consisting of solid water particles 102.

An initial Step 302 of the method 300 includes providing a cosmetic item 200, the cosmetic item 200 comprising substantially pure water 106 and at least one indigenous ingredient 104. In an alternative step, a consumable liquid 202 containing substantially pure water 106 and at least one indigenous ingredient 104 may also be obtained. In one embodiment, the cosmetic item 200 is a face mask or cream, and the consumable liquid is an herbal drink.

A Step 304 may include at least partially removing the substantially pure water 106 from the cosmetic item 200. In an alternative embodiment, a step may include removing the substantially pure water 106 from the consumable liquid 202. The cosmetic item 200 and the consumable liquid 202 initially contain a significant amount of pure water 106 in their makeup. However, in alternative embodiments of the present disclosure, the pure water 106 is not removed from the cosmetic item 200 or the consumable liquid 202.

However, in other embodiments, the composition 100 may be added to the cosmetic item 200 and the consumable liquid 202 without removing the pure water 106. For example, adding the solid water particle composition 100 to an alcoholic drink. By experiment the majority of consumers feels better taste, and probably healthier. Here, there is no removal of water 106 from the alcoholic drink.

Another example is adding the solid water particle composition 100 directly to gasoline. Here also, there is no removal of water 106 because there is little water in gasoline anyway. In yet another example, for a cosmetic face mask, the pure water 106 is removed there first in traditional cosmetic face mask before adding the solid water particle composition 100.

The method may further include a Step 306 of leaving the at least one indigenous ingredient 104 in the cosmetic item 200 substantially the same. Maintaining the status quo for the indigenous ingredient 104 is accomplished by minimizing manipulation to the cosmetic item 200 while adding a solid water particle composition 100, as described below. In an alternative embodiment, a step may include leaving the at least one indigenous ingredient 104 in the consumable liquid 202 substantially the same. The indigenous ingredient 104 may comprise any vitamin, herb, and solvent used in prior art ingredients for the cosmetic item 200 and the consumable liquid 202.

In one embodiment, a Step 308 includes adding a solid water particle composition 100 to the cosmetic item 200. In an alternative embodiment, a step may include adding a solid water particle composition 100 to the consumable liquid 202. The solid water particle composition 100 comprises solid water particles 102.

A final Step 310 comprises enhancing, through addition of the solid water particle composition 100, at least one health benefit from the cosmetic item 200. In an alternative embodiment, a step may include enhancing, through addition of the solid water particle composition, at least one health benefit from the consumable liquid 202. Thus in essence, the present invention substitutes the pure water 106 component of an indigenous material 104 with water consisting of solid water particles 102.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method of adding a solid water particle composition to a facial cosmetic item selected from the group consisting of face mask, face cream, and face gel, the method comprising:
   providing an original facial cosmetic item having pure water;
   removing the pure water in the facial cosmetic item;
   adding a solid water particle composition to the original facial cosmetic item to create an enhanced cosmetic item;
   wherein the original facial cosmetic item comprises at least one vitamin selected from the group consisting of vitamin C, vitamin B, and vitamin E, at least one plant selected from the group consisting of aloe vera and mulberry, at least one chemicals selected from the group consisting of titanium dioxide, potassium hydroxide, and sodium hydroxide, and at least one trace element selected from the group consisting of zinc and selenium.

2. The method of claim 1, wherein the original facial cosmetic item comprises at least one of the following: an anti-aging composition, an anti-wrinkle composition, an anti-oxidant composition, a plant extract, and an animal extract.

3. The method of claim 2, wherein the original facial cosmetic item is configured to provide a therapeutic effect on at least one of the following: gout, migraine, arthritis, joint problem, rheumatoid arthritis, tumor, neck pain, back pain, high level of cholesterol, high blood pressure, high sugar level, and a chronic disease.

* * * * *